(12) United States Patent
Wang

(10) Patent No.: US 11,366,123 B2
(45) Date of Patent: Jun. 21, 2022

(54) GLUCURONYLATION AS A NEW ACIDIC POST-TRANSLATIONAL MODIFICATION ON THERAPEUTIC MONOCLONAL ANTIBODIES

(71) Applicant: Regeneron Pharmaceuticals, Inc., Tarrytown, NY (US)

(72) Inventor: Shunhai Wang, Tarrytown, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 540 days.

(21) Appl. No.: 16/260,482

(22) Filed: Jan. 29, 2019

(65) Prior Publication Data

US 2019/0234964 A1 Aug. 1, 2019

Related U.S. Application Data

(60) Provisional application No. 62/624,338, filed on Jan. 31, 2018.

(51) Int. Cl.
*G01N 33/543* (2006.01)
*G01N 33/68* (2006.01)
*C07K 1/18* (2006.01)
*C07K 16/00* (2006.01)
*C07K 1/16* (2006.01)
*C07K 1/22* (2006.01)

(52) U.S. Cl.
CPC ........... *G01N 33/6857* (2013.01); *C07K 1/16* (2013.01); *C07K 1/18* (2013.01); *C07K 1/22* (2013.01); *C07K 16/00* (2013.01); *C12Y 304/2201* (2013.01); *C07K 2317/40* (2013.01); *C07K 2317/52* (2013.01); *C07K 2317/55* (2013.01); *G01N 2333/96413* (2013.01); *G01N 2440/00* (2013.01)

(58) Field of Classification Search
None
See application file for complete search history.

(56) References Cited

FOREIGN PATENT DOCUMENTS

| AU | 2019213647 A1 | 7/2020 |
| CA | 3084181 A1 | 8/2019 |
| TW | 201940884 A | 10/2019 |
| WO | 20170120613 | 7/2017 |
| WO | 2019/152356 A2 | 8/2019 |

OTHER PUBLICATIONS

Goetze et al., Rapid LC-MS screening for IgG Fc modifications and allelic variants in blood, Molecular Immunology, 49, 2011, pp. 338-352. (Year: 2011).*
Wagner-Rousset et al., Development of a fast workflow to screen the charge variants of therapeutic antibodies, Journal of Chromatography A, 1498, pp. 147-154. (Year: 2017).*
Leblanc et al., Charge variants characterization of a monoclonal antibody by ion exchange chromatography couple on-line to native mass spectrometry: Case study after a long-term storage, Journal of Chromatography B, 1048, pp. 130-139. (Year: 2017).*
Brady et al., Characterization of nonenzymatic glycation on a monoclonal antibody, Anal. Chem., 2007, 79, pp. 9403-9413. (Year: 2007).*
Haraguchi et al., Immunofluorescence technique for 100 nm-thick semithin sections of Epon-embedded tissues, Histochem Cell Biol (2002), 117, pp. 81-85. (Year: 2002).*
FlyBase webpage, "The modification of a protein by amino acid glucuronylation, the addition of a glucuronate group, the uronic acid derived from glucose", Database accession No. GO:0018321, Jan. 11, 2019.
ZFIN webpage, "Protein glucuronylation", Database accession No. GO:0018321, http://zfin.org/action/ontology/term-detail/GO:0018321, Jul. 26, 2019.
ZFIN webpage, "Protein glycosylation", Database accession No. GO:0006486, http://zfin.org/action/ontology/term-detail/GO:0006486, Jul. 26, 2019.
The partial international search and preliminary opinion of the ISA, dated Jul. 17, 2019.

* cited by examiner

*Primary Examiner* — Gary Counts
(74) *Attorney, Agent, or Firm* — McCarter & English, LLP; John P. Isacson

(57) ABSTRACT

Compositions and methods for identifying glucuronylated protein drug products are provided.

6 Claims, 17 Drawing Sheets

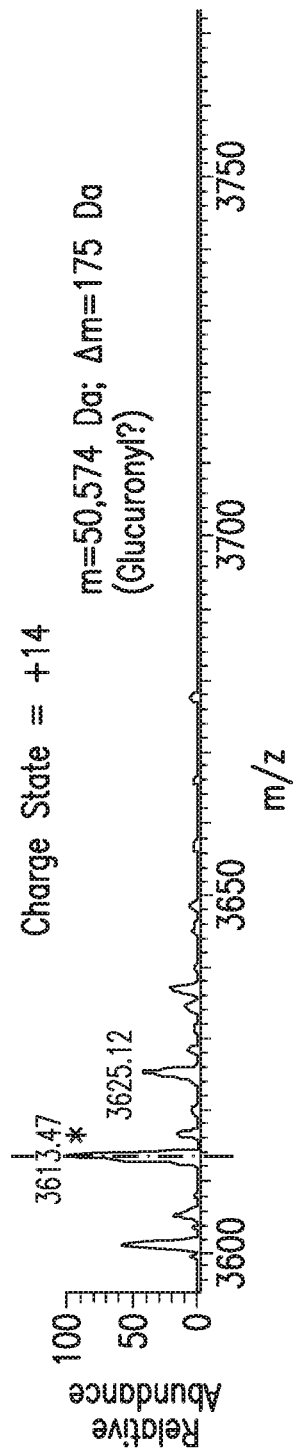
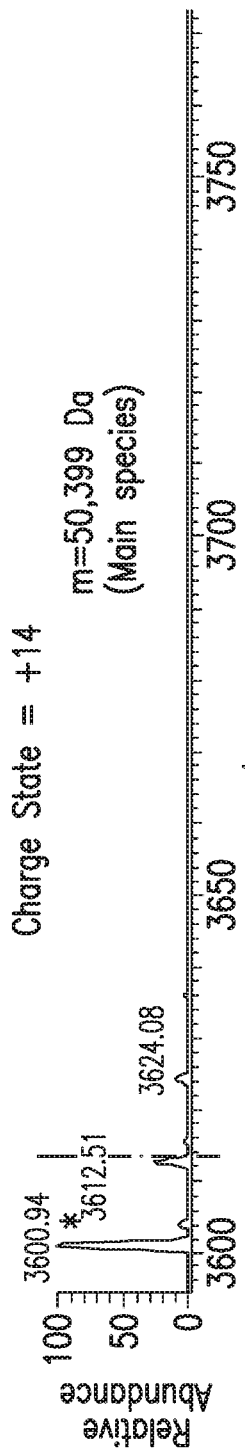
FIG. 1O
FIG. 1P

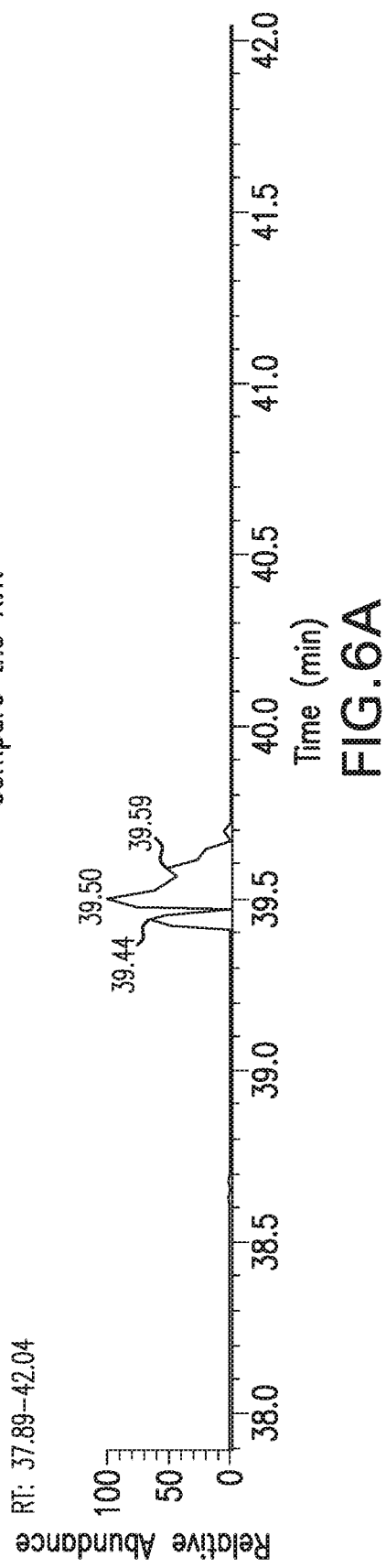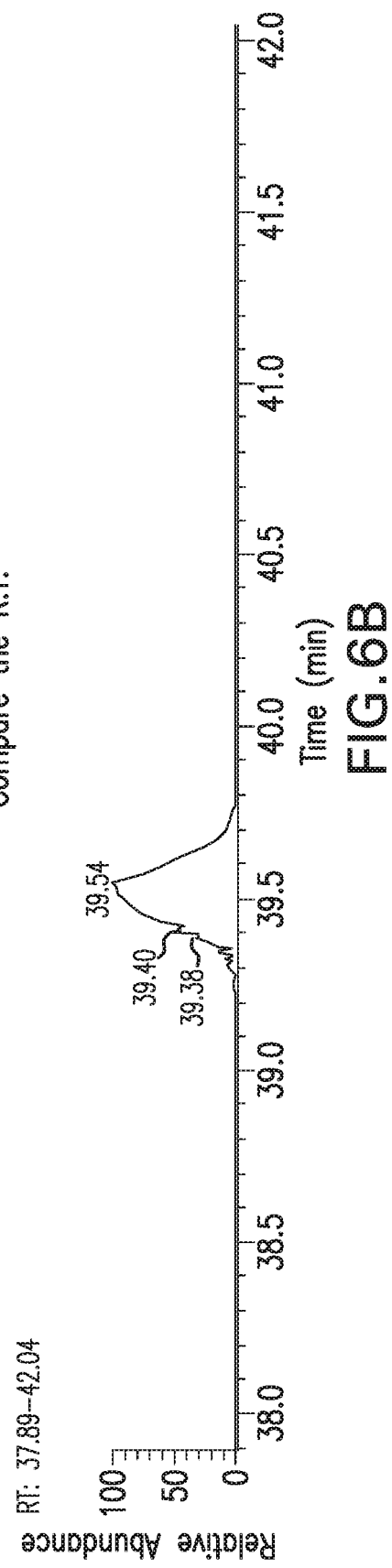

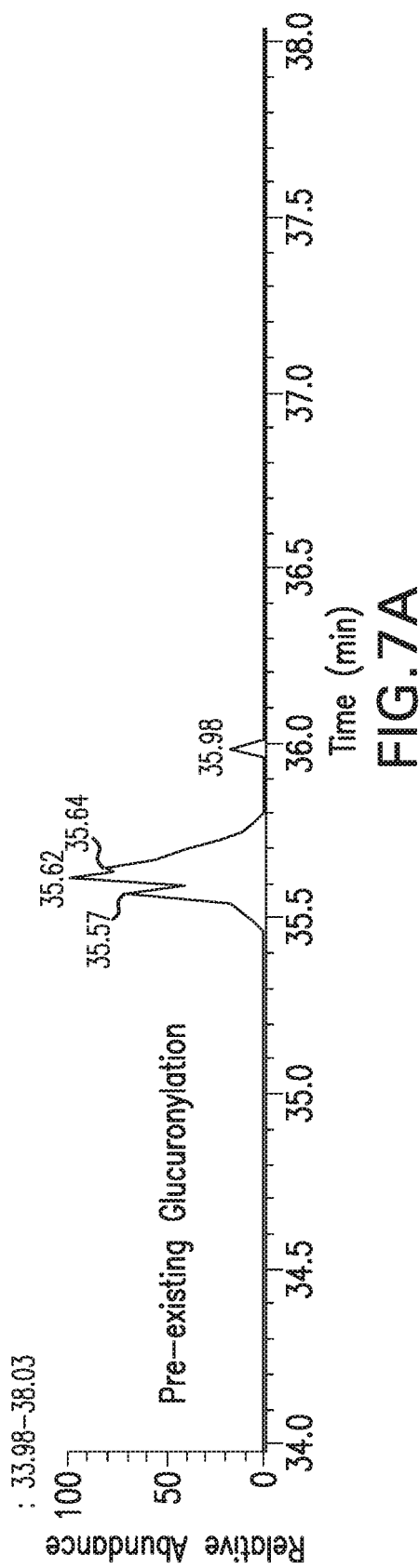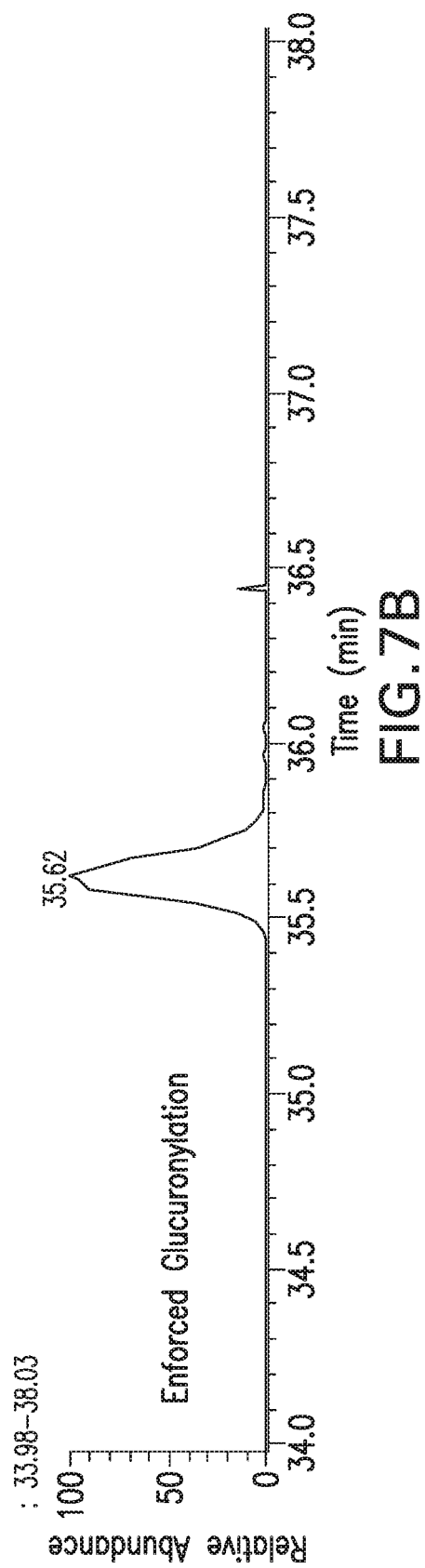

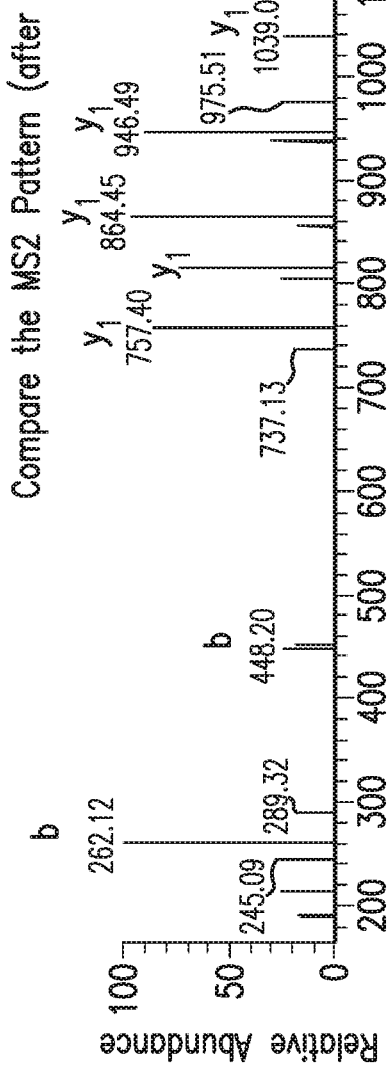
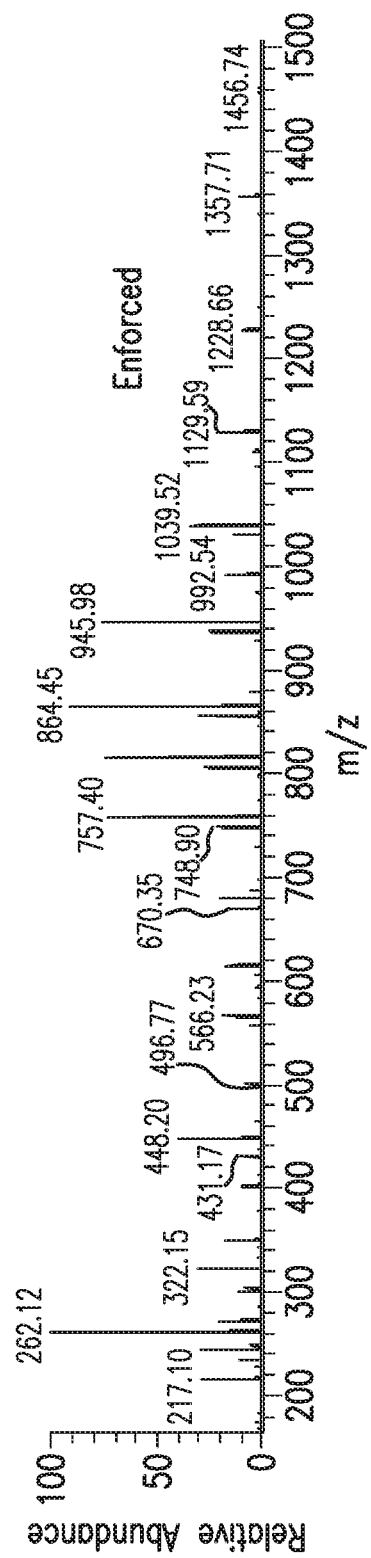
FIG.7C
FIG.7D

GLUCURONYLATION AS A NEW ACIDIC POST-TRANSLATIONAL MODIFICATION ON THERAPEUTIC MONOCLONAL ANTIBODIES

CROSS-REFERENCE TO RELATED APPLICATIONS

This application claims benefit of and priority to U.S. Provisional Patent Application No. 62/624,338 filed on Jan. 31, 2018, which is incorporated by reference in its entirety.

FIELD OF THE INVENTION

The invention is generally related to systems and methods to identify post-translational modifications on therapeutic proteins.

BACKGROUND OF THE INVENTION

In the pharmaceutical industry, recombinant monoclonal antibodies (mAbs) constitute a major class of protein therapeutics. Changes to mAb structure may influence therapeutic efficacy, bio-availability and clearance, and immunogenic properties of therapeutic mAbs.

Additionally, changes in mAbs could alter drug safety and efficacy. Comprehensive characterization of the primary structure, post-translational modifications (PTMs), and disulfide linkages of mAbs is critical to the evaluation of drug efficacy and safety, as well as understanding the structure/function relationships.

Among various assays used to ensure product and process consistency, ion exchange chromatography (IEX) is a commonly used technique to assess the charge heterogeneity of mAb molecules. mAb charge variants may frequently be attributed to post-translational modifications (PTMs) that can alter the surface charge of the mAb molecule. Due to the ever-advancing LC-MS technique, many known or novel PTMs have been identified. Additionally, their contributions to charge heterogeneity have been elucidated. While advances in technology have provided numerous novel PTMs, there is still a need to further characterize and discover PTMs that alter mAb activity and stability.

It is therefore an object of the invention to provide systems and methods for identifying PTMs.

SUMMARY OF THE INVENTION

Compositions and methods for identifying glucuronylated protein drug products are provided. One embodiment provides a method for identifying glucuronylation of a protein drug product by deglycosylating the protein drug product and treating the deglycosylated protein drug product with an enzyme, for example FabRICATOR®, to produce one Fc* fragment (two identical Fc/2 fragments bound together through non-covalent interactions) and one $Fab_2$. The Fc* and $Fab_2$ fragments are then separated into acidic fractions of Fc* and $Fab_2$. In one embodiment the Fc* and $Fab_2$ fragments are separated using ion exchange chromatography, for example strong cation exchange chromatography. Once separated, the acidic fractions are, collected, dried and denatured. The dried and denatured acidic fractions are alkylated and then digested with trypsin to form a sample. The sample is then treated with $NaBH_4$ to form a reduced sample. Both reduced Fc* and reduced $Fab_2$ samples are then subjected to reverse phase liquid chromatography/mass spectroscopy analysis to identify glucuronylation of the protein drug product. In one embodiment, the method includes the step of comparing mass spectroscopy results between the reduced sample and non-reduced sample to identify mass differences between the reduced and non-reduced samples. The drug product can be a monoclonal antibody or a fusion protein. In one embodiment, glucuronylation is detected on lysine residues of the protein drug product.

In one embodiment the Fc* and $Fab_2$ fragments are formed using a recombinantly modified form of IdeS from *Streptocoocus pyogenes* sold under the name FabRICATOR®.

The disclosed method can be used to monitor the purity of protein drug products, for example monoclonal antibodies or other therapeutic proteins. One embodiment provides a method for increasing purity of a protein drug product by analyzing the protein drug product to identify glucuronylation on a primary amine of one or more amino acids of the protein drug product and removing glucuronylated proteins from the protein drug product to produce a purified protein drug product. Glucuronylation can be detected using the methods described above and in the Examples. In one embodiment, the glucuronylated proteins are detected by high performance liquid chromatography techniques optionally coupled with mass spectroscopy. Representative chromatography techniques include, but are not limited to size exclusion chromatography, ion exchange chromatography, affinity chromatography, high performance liquid chromatography, ultra performance liquid chromatography, and combinations thereof. Typically, the glucuronylation occurs on a lysine residue of the protein drug product.

Another embodiment provides a method for identifying post-translationally modified protein drug product by assaying a protein drug product obtained from a mammalian cell culture for glucuronylation, wherein the presence of glucuronylation of the protein drug product indicates that the protein drug product comprises post-translational modifications. The mammalian cell culture typically contains Chinese Hamster Ovary cells.

Still another embodiment provides a protein drug product containing a therapeutic protein, wherein less than 1.0%, 2.0%, 3.0%, 4.0%, 5.0%, 6.0%, 7.0%, 8.0%, 9.0%, or 10% of the therapeutic protein's amino acids are glucuronylated. In one embodiment, the amino acid is lysine. Typically, the therapeutic protein is a monoclonal antibody, recombinant protein, or fusion protein.

BRIEF DESCRIPTION OF THE DRAWINGS

FIGS. 1G-1P are chromatograms showing Fc charge variant analysis for an exemplary mAb.

FIG. 6A is a chromatogram from a second sample. 6B is a chromatogram from the second sample treated with glucuronic acid showing forced glucuronylation.

FIG. 7A is a chromatogram from a third sample. 7B is a chromatogram from the third sample treated with glucuronic acid showing forced glucuronylation. FIG. 7C shows the results of M2 fragmentation patterns for pre-existing glucuronylation. FIG. 7D shows the results of M2 fragmentation patterns for samples treated with glucuronic acid.

DETAILED DESCRIPTION OF THE INVENTION

I. Definitions

Figure 1A:
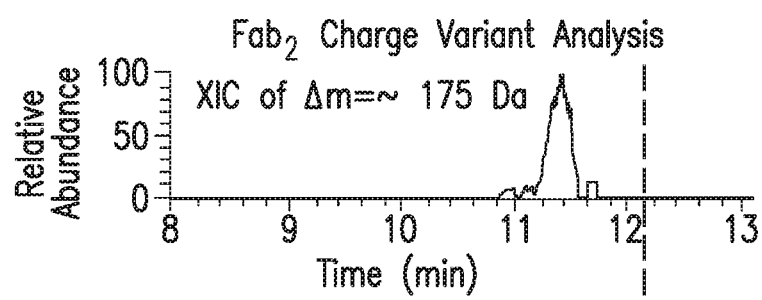
FIGS. 1A-1F are chromatograms showing $Fab_2$ charge variant analysis for an exemplary mAb.
Figure 1B:
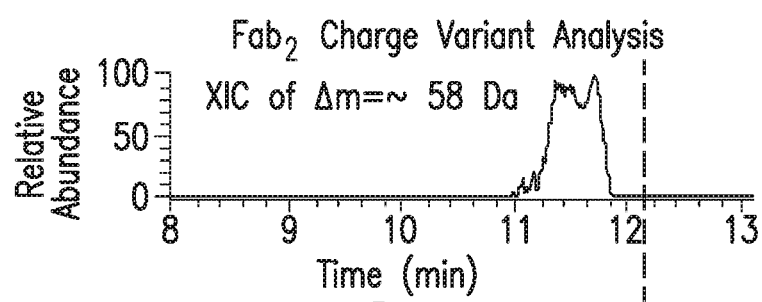
Figure 1C:
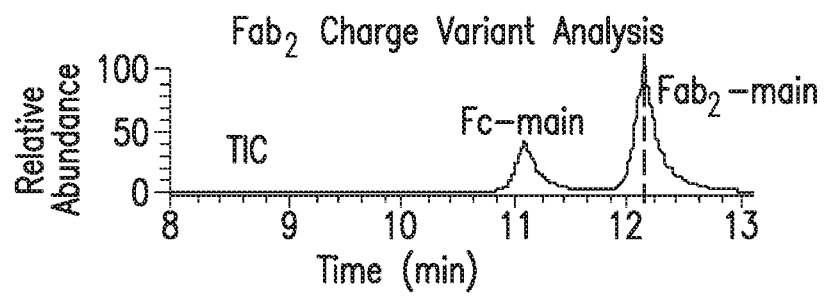
Figure 1D:
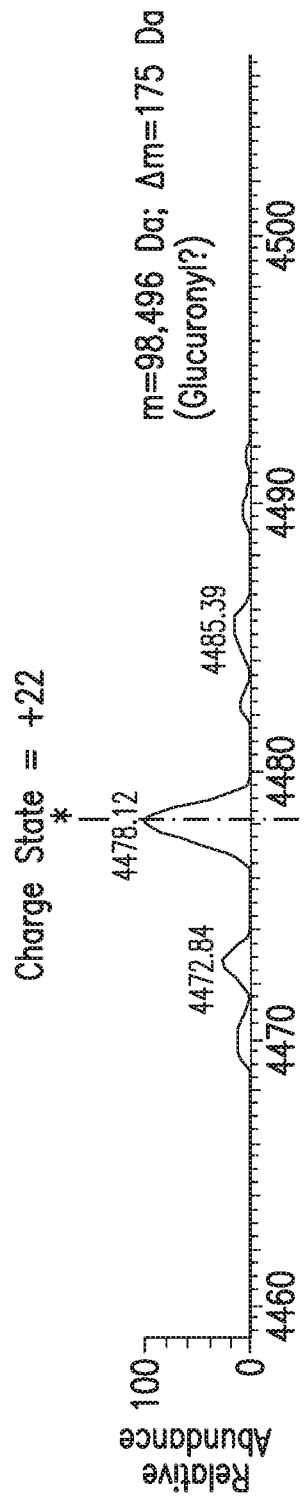
Figure 1E:
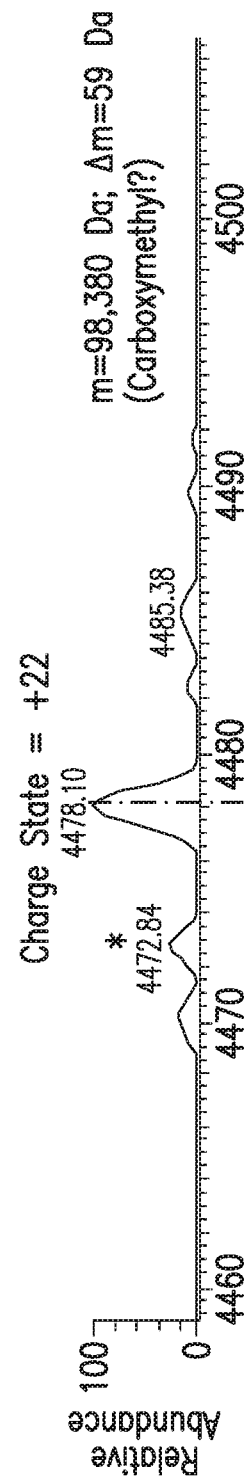
Figure 1F:
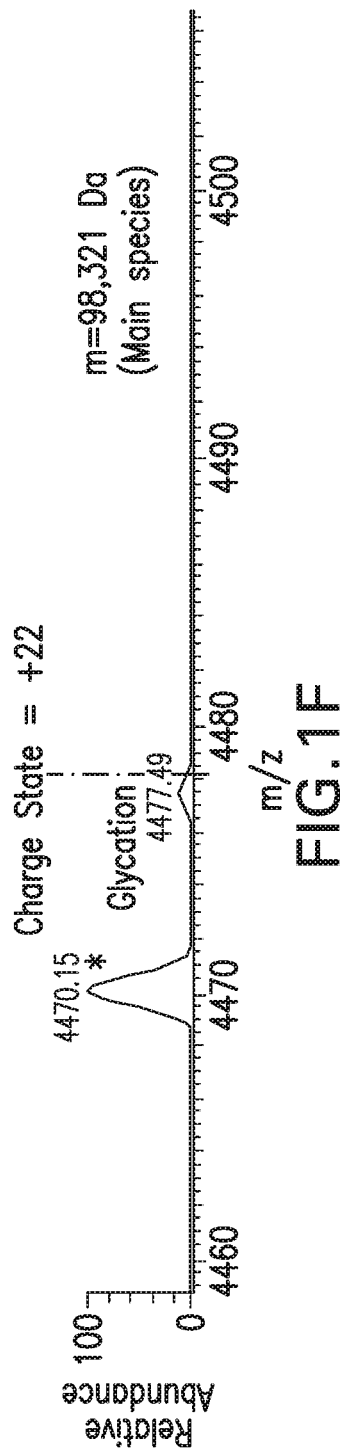
Figure 1G:
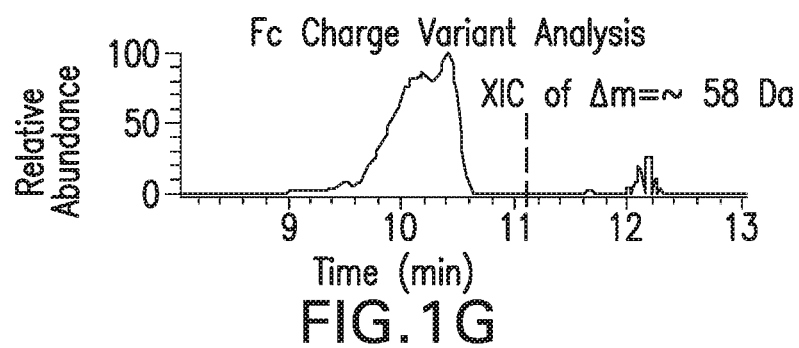
Figure 1H:
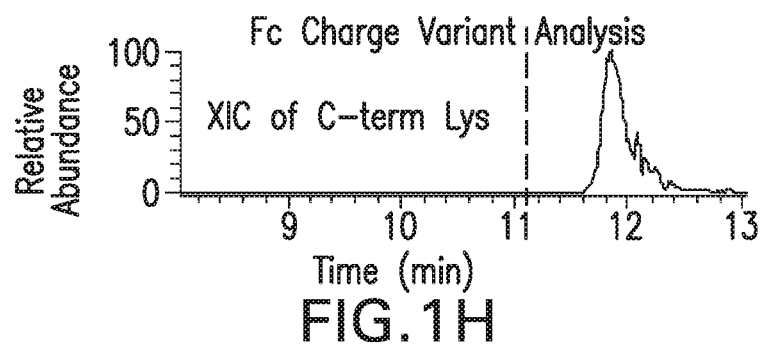
Figure 1I:
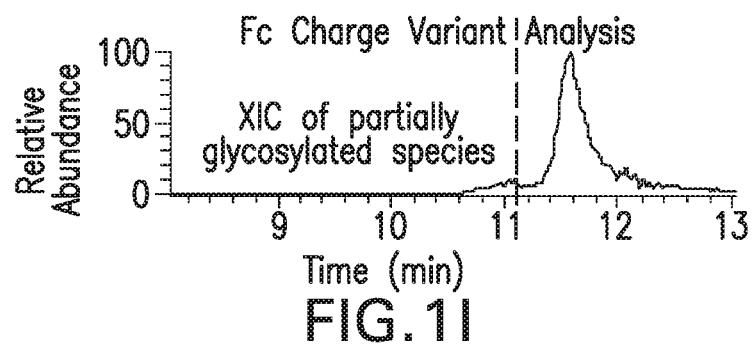
Figure 1J:
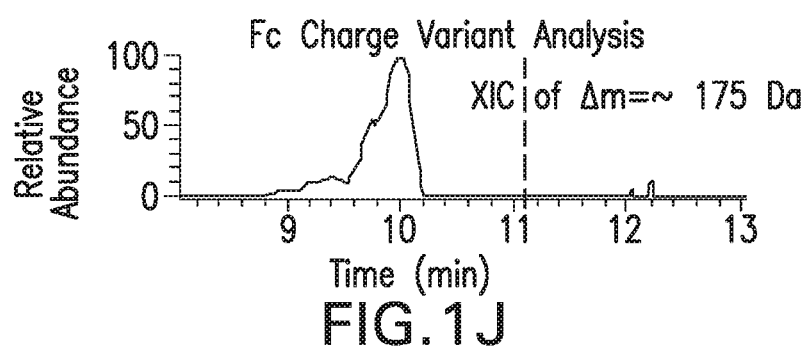
Figure 1K:
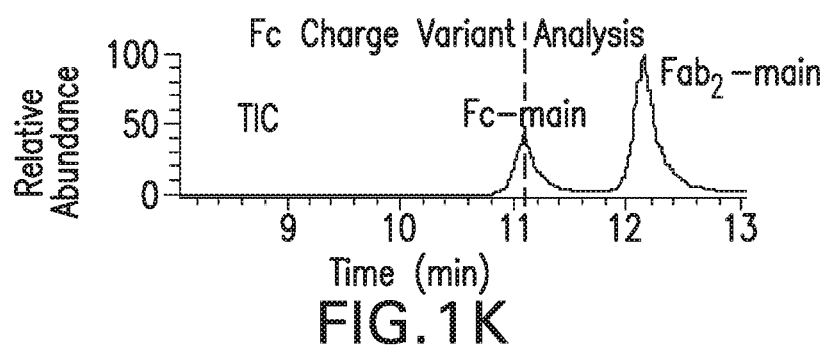
Figure 1L:
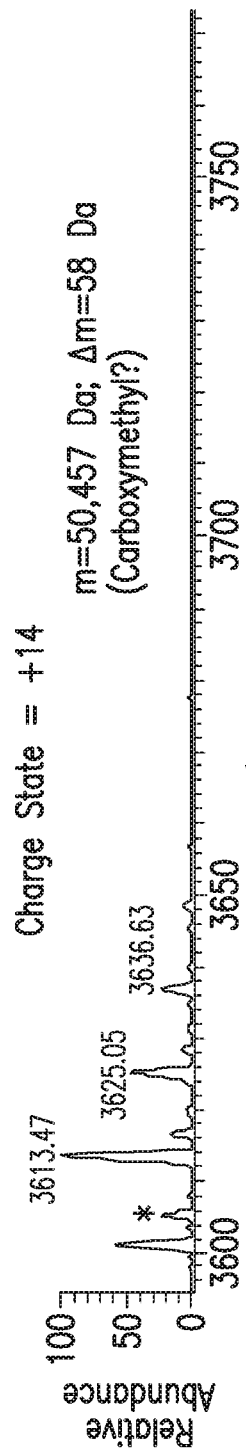
Figure 1M:
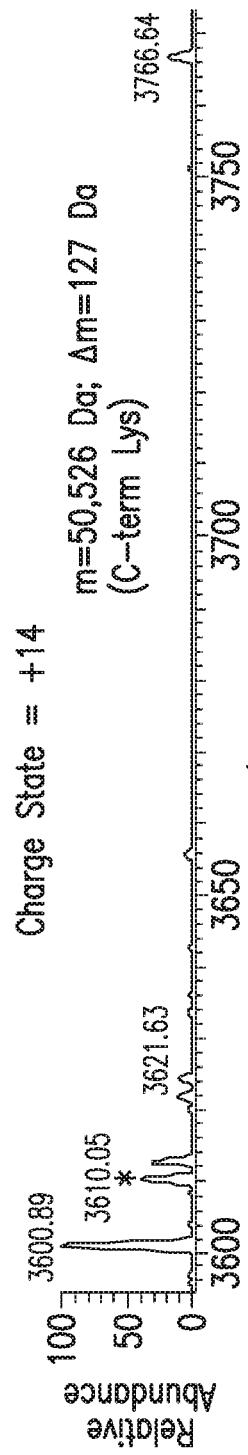
Figure 1N:
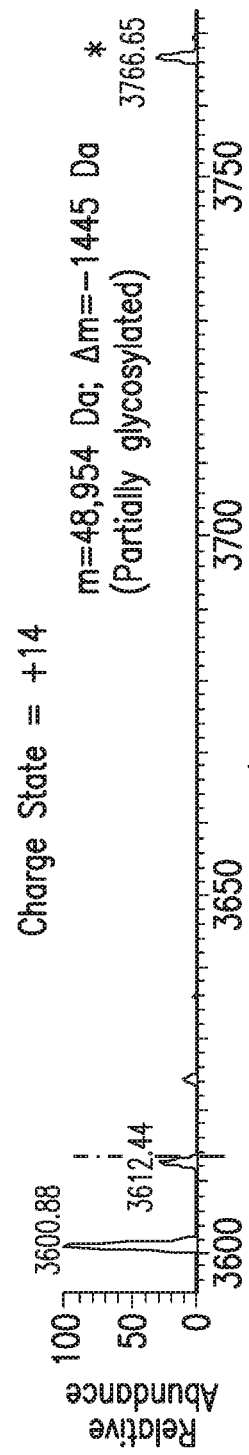

As used herein, the term "antibody" is intended to denote an immunoglobulin molecule that possesses a "variable region" antigen recognition site. The term "variable region" is intended to distinguish such domain of the immunoglobulin from domains that are broadly shared by antibodies (such as an antibody Fc domain). The variable region includes a "hypervariable region" whose residues are responsible for antigen binding. The hypervariable region includes amino acid residues from a "Complementarity Determining Region" or "CDR" (i.e., typically at approximately residues 24-34 (L1), 50-56 (L2) and 89-97 (L3) in the light chain variable domain and at approximately residues 27-35 (H1), 50-65 (H2) and 95-102 (H3) in the heavy chain variable domain; Kabat et al., Sequences of Proteins of Immunological Interest, 5th Ed. Public Health Service, National Institutes of Health, Bethesda, Md. (1991)) and/or those residues from a "hypervariable loop" (i.e., residues 26-32 (L1), 50-52 (L2) and 91-96 (L3) in the light chain variable domain and 26-32 (H1), 53-55 (H2) and 96-101 (H3) in the heavy chain variable domain, Chothia and Lesk, 1987, J. Mol. Biol. 196:901-917). "Framework Region" or "FR" residues are those variable domain residues other than the hypervariable region residues as herein defined.

As used herein, "monoclonal antibody (mAb) refers to an antibody that is made by identical immune cells that are all clones of a unique parent cell that specifically bind a target substance. mAbs have become increasingly popular as therapeutics for a variety of diseases, including but not limited to cancers, arthritis, asthma, colitis, autoimmune diseases, and infections. mAbs are large protein with molecular weights near 150 kDa and are composed of two identical ~50 kDa heavy chains (HC) and two identical ~25 kDa light chains (LC). They also contain at least 16 disulfide bonds that maintain three-dimensional structure and biological activity. Although sharing similar secondary protein structures, different mAbs differ greatly in the sequence of variable regions, especially in the complementarity determining regions (CDRs) which are responsible for the diversity and specificity of antibody-antigen binding.

As used herein, the term "antigen binding fragment" of an antibody refers to one or more portions of an antibody that contain the antibody's Complementarity Determining Regions ("CDRs") and optionally the framework residues that include the antibody's "variable region" antigen recognition site, and exhibit an ability to immunospecifically bind antigen. Such fragments include Fab', F(ab')2, Fv, single chain (ScFv), and mutants thereof, naturally occurring variants, and fusion proteins including the antibody's "variable region" antigen recognition site and a heterologous protein (e.g., a toxin, an antigen recognition site for a different antigen, an enzyme, a receptor or receptor ligand, etc.).

As used herein, "ion exchange chromatography (IEX)" refers to a method of separating ionizable molecules based on their total charge. Proteins are made up of both positively and negatively charged chemical groups. Depending on the pH of the environment, proteins can carry a net positive charge, a net negative charge, or no charge. The pH at which the molecule has no net charge is called the isoelectric point (pI). The net charge of a protein of interest is calculated by combining the isoelectric point, which can be calculated based on the primary sequence of the molecule, and the pH of the buffer. When an IEX column is loaded with a sample at a particular pH, all proteins that are appropriately charged will bind the resin in the column. For example, a protein with a net negative charge will be captured by an anion exchange resin column.

As used herein, "charge variants" refer to isoforms and protein variants with altered isoelectric point (pI), or charge, compared to the unmodified form. Charge variants with relatively lower pI are referred to as "acidic variants" while charge variants with relatively higher pI are referred to as "basic variants". Charge variants can influence properties of antibodies, including changing the ability of mAbs to bind proteins or cell membrane targets. This can affect the tissue penetration, tissue distribution, and pharmacokinetics of the antibodies. Examples of charge variants include but are not limited to deamidation, formation of N-terminal pyroglutamate, aggregation, isomerization, sialylated glycans, antibody fragmentation, and glycation at the lysine residues.

As used herein, "post-translational modification (PTM)" refers to biochemical modifications that occur to one or more amino acids on a protein following protein biosynthesis. PTM plays a major role in cellular function through regulating protein folding, targeting proteins to specific cellular compartments, or through regulating the interaction between ligands and other proteins. The most common modifications are the specific cleavage of precursor proteins; formation of disulfide bonds, or covalent addition or removal of low-molecular-weight groups, thus leading to modifications such as acetylation, amidation, biotinylation, cysteinylation, deamidation, farnesylation, formylation, geranylation, glutathionylation, glycation (nonenzymatic conjugation with carbohydrates), glycosylation (enzymatic conjugation with carbohydrates), hydroxylation, methylation, mono-ADP-ribosylation, myristoylation, oxidation, palmitoylation, phosphorylation, poly(ADP-ribosyl)ation, stearoylation, or sulfation. Ubiquitilation is another common PTM that is important in protein degradation pathways. Some PTM are reversible by the action of deconjugating enzymes.

As used herein, "N-linked glycosylation" refers to a post-translational protein modification. N-linked glycosylation is the attachment of oligosaccharides to a nitrogen atom, usually the N4 of asparagine residues. All N-linked carbohydrates are linked through N-Acetylglucosamine and the amino acid asparagine.

As used herein, "peptide mapping" refers to the technique of characterizing proteins and elucidating their primary amino acid structures. It is a widely utilized technique to characterize monoclonal antibodies and other recombinant protein pharmaceuticals.

As used herein, "glucuronidation" refers to a conjugation reaction wherein glucuronic acid derived from cofactor UDP-glucuronic acid is covalently linked to a substrate containing a nucleophilic functional group.

II. Methods for Identifying Glucuronylation and Methods of Use Thereof

A. Identifying Glucuronylation

Compositions and methods for identifying glucuronylated protein drug products are provided. Examples 1-3 provide a detailed description of the methods that are used to detect and identify glucuronylated amino acids in therapeutic proteins. Generally, one method for identifying glucuronylation of a protein drug product includes deglycosylating the protein drug product and treating the deglycosylated protein drug product with FabRICATOR® to produce one Fc* fragment (two identical Fc/2 fragments bound together through non-covalent interactions) and one Fab$_2$ fragment. In one embodiment the Fc* and Fab$_2$ fragments are produced using a recombinant IdeS enzyme from *Streptocoocus pyogenes* sold under the name FabRICATOR®.

The Fc* and Fab$_2$ fragments are then separated into acidic fractions of Fc* and Fab$_2$. In one embodiment the Fc* and Fab$_2$ fragments are separated using ion exchange chromatography, for example strong cation exchange chromatography. As described in the Example 1 an aliquot of the deglycosylated mAb sample (~50 μg) was injected onto a YMC-BioPro SP-F strong cation exchange (SCX) column (100×4.6 mm) coupled to a Thermo Exactive Plus EMR mass spectrometer or a Thermo Q Exactive plus mass spectrometer for mass measurement. The samples were separated and eluted over a 20 minute pH gradient with ammonium acetate based buffers (buffer A: 20 mM ammonium acetate, pH 5.8; buffer B: 200 mM ammonium acetate, pH 7.6). An analytical splitter (~200:1 ratio) was connected after the SCX column to reduce the analytical flow to ~2 μL/min prior to the mass spectrometer for mass detection. The high flow from the splitter was diverted to a Waters ACQUITY photodiode array (PDA) detector for simultaneous UV detection (280 nm). As a result, an acidic shoulder peak was detected and attributed to a variant of the antibody with a mass increase of approximately 176 Da.

Once separated, the acidic fractions are collected, dried, and denatured. In one embodiment the collected acidic fractions are first dried in a SpeedVac™ and then denatured and reduced in 20 μL of solution containing 5 mM Dithiothreitol (DTT), 8 M urea and 100 mM Tris-HCl (pH 7.5) by heating at 50° C. for 30 minutes. It will be appreciated that one of skill in the art would understand that other reducing agents, denaturing agents, and temperatures can be used to dry and denature the acidic fractions.

The dried and denatured acidic fractions are alkylated and then enzymatically digested, for example with trypsin, to form a sample. The acidic fractions can be alkylated by incubating them in 10 mM iodoacetamide (IAA) at room temperature in the dark for 30 minutes. Digestion of the fractions can be accomplished by diluting them with 175 μL of 100 mM Tris-HCl (pH 7.5) and adding trypsin at enzyme-to-substrate ratio of 1:10 (w/w) at 37° C. for 4 hours.

The trypsin digested acidic fraction is then incubated with 50 mM NaBH$_4$ at 37° C. for 1 hour before quenching with 10% formic acid (FA) to form a reduced sample. The reduced sample is then subjected to reverse phase liquid chromatography/mass spectroscopy analysis to identify glucuronylation of the protein drug product. In one embodiment, the method includes the step of comparing mass spectroscopy results between the reduced sample and non-reduced sample to identify mass differences between the reduced and non-reduced samples. The drug product can be a monoclonal antibody or a fusion protein. In one embodiment, glucuronylation is detected on lysine residues of the protein drug product.

B. Methods for Increasing Purity of Protein Drug Products

The disclosed methods can be used to monitor the purity of protein drug products, for example monoclonal antibodies or other therapeutic proteins. One embodiment provides a method for increasing purity of a protein drug product by analyzing the protein drug product to identify glucuronylation on a primary amine of one or more amino acids of the protein drug product and removing glucuronylated proteins from the protein drug product to produce a purified protein drug product. Glucuronylation can be detected using the methods described above and in the Examples. In one embodiment, the glucuronylated proteins are removed by high performance liquid chromatography techniques optionally coupled with mass spectroscopy. Representative chromatography techniques include, but are not limited to size exclusion chromatography, ion exchange chromatography, affinity chromatography, high performance liquid chromatography, ultra performance liquid chromatography, and combinations thereof. Typically, the glucuronylation occurs on a lysine residue of the protein drug product.

Another embodiment provides a method for identifying post-translationally modified protein drug product by assaying a protein drug product obtained from a mammalian cell culture for glucuronylation, wherein the presence of glucuronylation of the protein drug product indicates that the protein drug product comprises post-translational modifications. The mammalian cell culture typically contains Chinese Hamster Ovary cells.

C. Protein Drug Products

Still another embodiment provides a protein drug product containing a therapeutic protein, wherein less than 1.0%, 2.0%, 3.0°%, 4.0%, 5.0%, 6.0%, 7.00, 8.0%, 9.0%, or 10% of the therapeutic protein's amino acids are glucuronylated. The percent glucuronylation can be determined using the disclosed methods. In one embodiment, the amino acid is lysine. Typically, the therapeutic protein is a monoclonal antibody or fusion protein.

The protein drug product can be an antibody or an antigen binding fragment thereof, an recombinant protein, or a fusion protein. The antibody is preferably a monoclonal antibody.

EXAMPLES

Example 1: Identification of Modifications at Antibody Intact Level

Methods mAbs were subjected to online IEX-MS analysis. An aliquot of the deglycosylated mAb sample (~50 μg) was injected onto a YMC-BioPro SP-F strong cation exchange (SCX) column (100×4.6 mm) coupled to a Thermo Exactive Plus EMR mass spectrometer or a Thermo Q Exactive plus mass spectrometer for mass measurement. The samples were separated and eluted over a 20 minute pH gradient with ammonium acetate based buffers (buffer A: 20 mM ammonium acetate, pH 5.8; buffer B: 200 mM ammonium acetate, pH 7.6). An analytical splitter (~200:1 ratio) was connected after the SCX column to reduce the analytical flow to ~2 µL/min prior to the mass spectrometer for mass detection. The high flow from the splitter was diverted to a Waters ACQUITY photodiode array (PDA) detector for simultaneous UV detection (280 nm).

Results

As a result, an acidic shoulder peak was detected and attributed to a variant of the antibody with a mass increase of approximately 176 Da. However, the mass measurement at the intact level was not accurate because of complications from a glycation modification which elutes in the same acidic shoulder peak and is close in mass (162 Da).

Example 2: Detection of the New Acidic Modification at Antibody Sub-Domain Level Methods To increase the resolution of the acidic peak to the main peak and to improve the mass measurement accuracy, the deglycosylated mAb sample was treated with FabRICATOR, an enzyme that cleaves the heavy chain at the C-terminal of the two hinge region disulfide bonds.

Results

This treatment resulted in the generation of one $Fab_2$ fragment and two identical Fc/2 fragments that bound together through non-covalent interactions (Fc*). An aliquot of the digest was subjected to online IEX-MS analysis as described above. As expected, the same acidic variant with a mass increase of ~176 Da was detected in the acidic peaks of both Fab2 and Fc* (FIG. 1A-1P).

Example 3: Identification and Confirmation of the New Acidic Modification

Methods

To further identify the modification sites to amino acid residues and to obtain the accurate mass of this unknown modification, acidic fractions of the Fc* and Fab2 fragments were collected from the SCX column for peptide mapping analysis. The collected acidic fractions were first dried in a SpeedVac and then denatured and reduced in 20 µL of solution containing 5 mM Dithiothreitol (DTT), 8 M urea and 100 mM Tris-HCl (pH 7.5) by heating at 50° C. for 30 minutes. The samples were then alkylated with 10 mM iodoacetamide (IAA) by incubating at room temperature in the dark for 30 minutes. The reduced and alkylated samples were then diluted with 175 µL of 100 mM Tris-HCl (pH 7.5) and digested with trypsin at enzyme-to-substrate ratio of 1:10 (w/w) at 37° C. for 4 hours. The digestion was stopped by addition of 4 µL of 10% FA. Aliquots of each digested protein sample were then separated by RP-UPLC followed by on-line MS analysis. MS and MS/MS experiments were conducted on a Thermo Q Exactive Plus MS system with higher-energy collisional dissociation (HCD) employed for peptide fragmentation during MS/MS experiments. The MS raw data files were then searched against a database containing the mAb sequence and a variable wildcard modification of between 170 to 180 Da in mass.

Results

Figure 2:
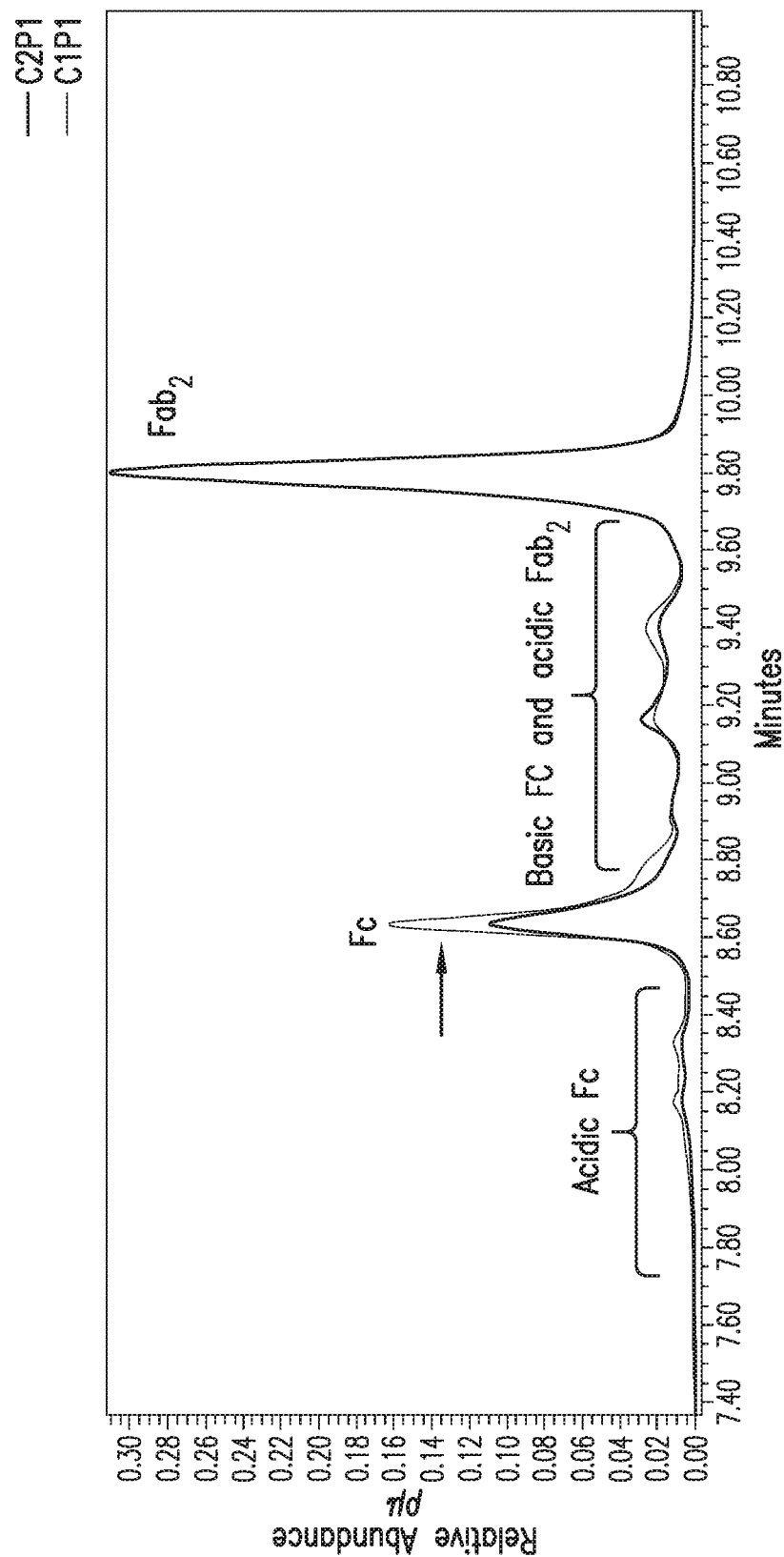
FIG. 2 is a chromatogram showing acidic Fc, basic Fc and acidic $Fab_2$ separation.

The results showed that this unknown modification exhibited a monoisotopic mass of +176.03 Da and occurred at low levels on multiple Lys residues in the mAb sequence (FIG. 2). Based on the accurate delta mass, this modification was hypothesized to have had the same elemental composition ($C_6H_8O_6$) as glucuronidation, which, however, was reported to occur on Ser and Thr via O-linkage catalyzed by UDP-glucuronosyltransferase.

Figure 3A:
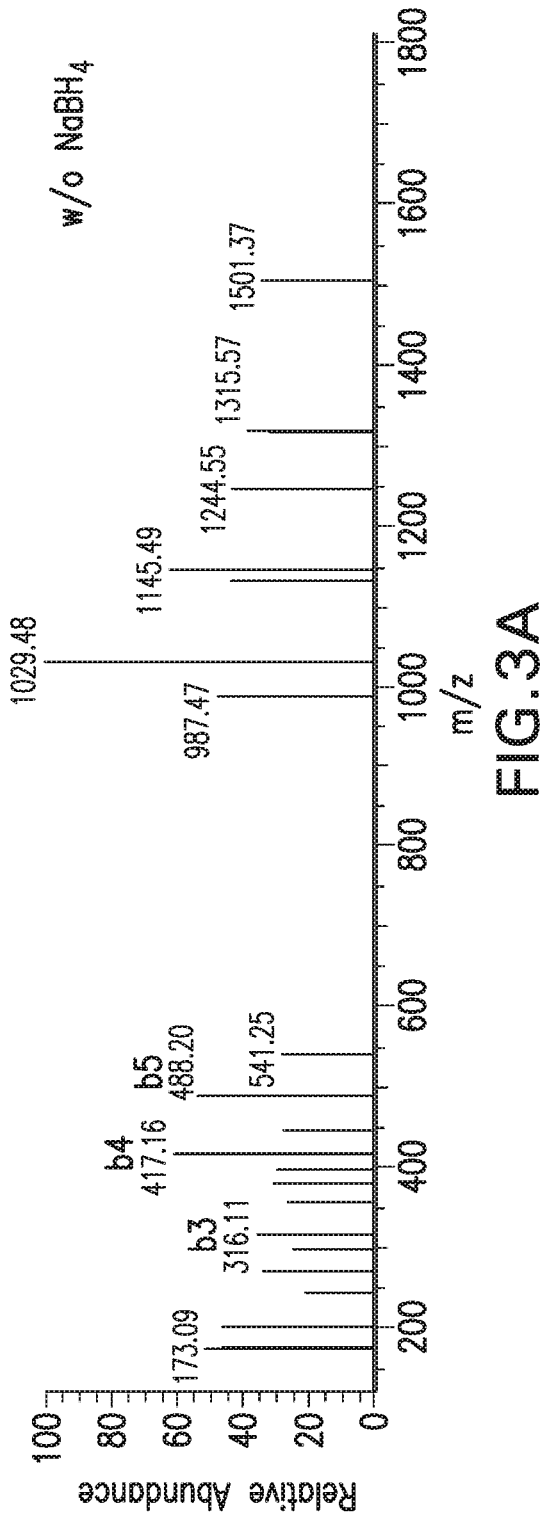
FIG. 3A shows MS2 fragmentation patterns for samples without $NaBH_4$ treatment.
Figure 3B:
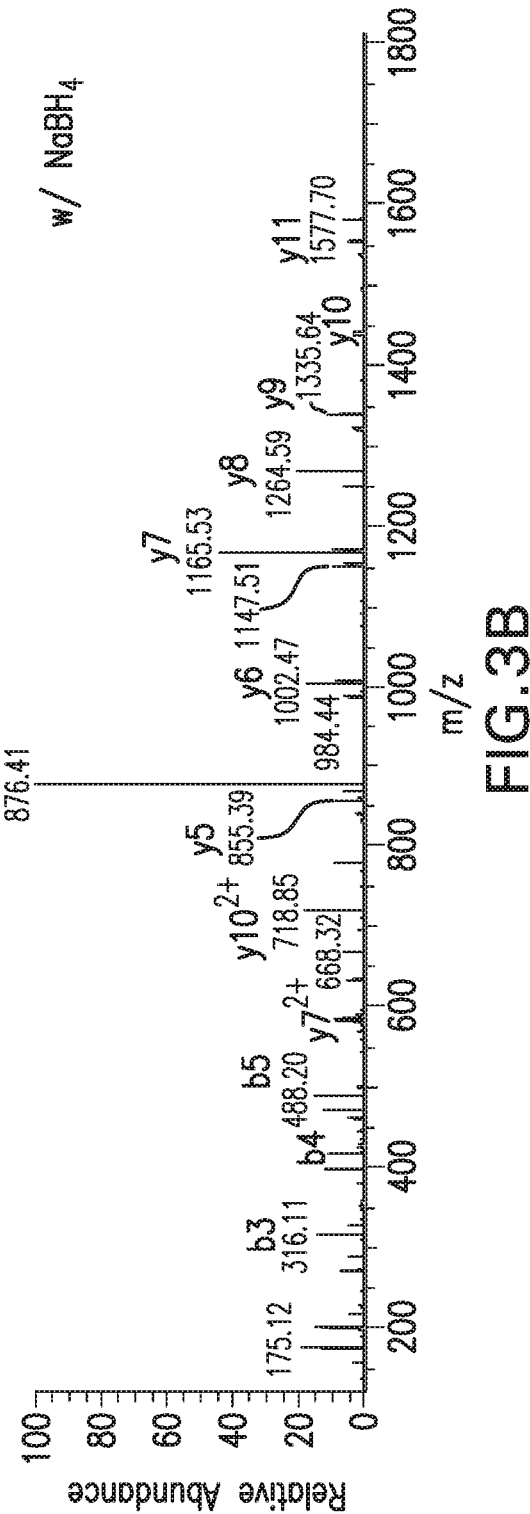
FIG. 3B shows MS2 fragmentation patterns for samples with $NaBH_4$ treatment.
Figure 4A:
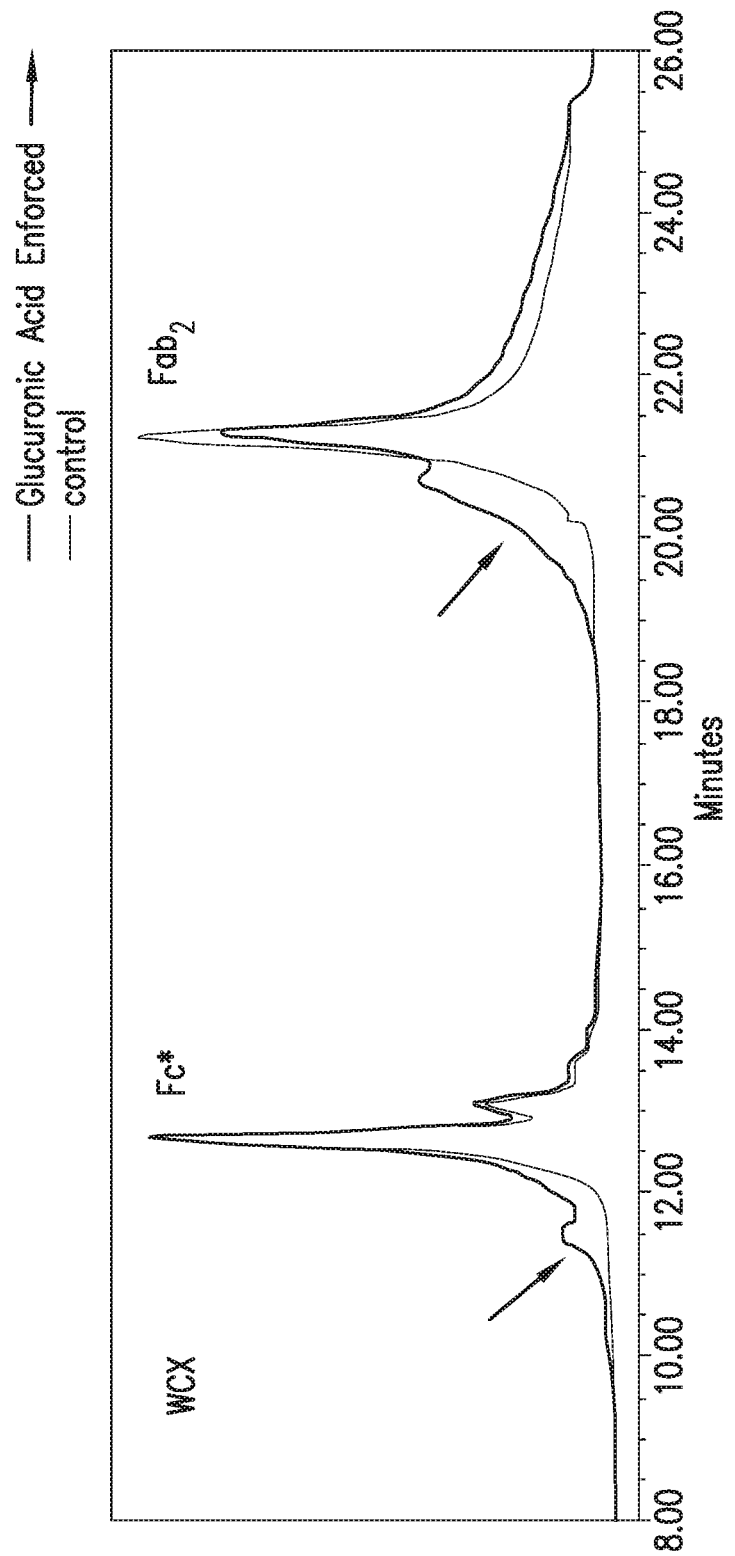
FIG. 4A is a chromatogram using a WCX column. Arrow indicates forced glucuronic acid treatment.
Figure 4B:
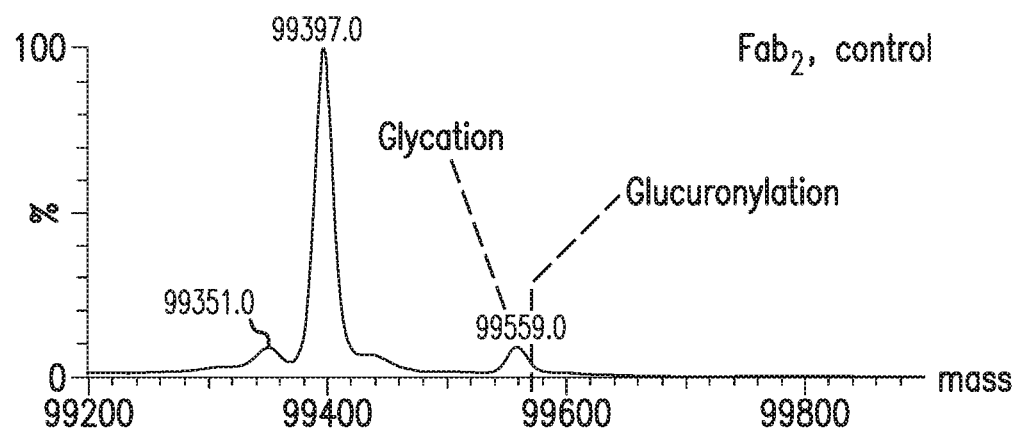
FIG. 4B is a graph showing results of $Fab_2$ control.
Figure 4C:
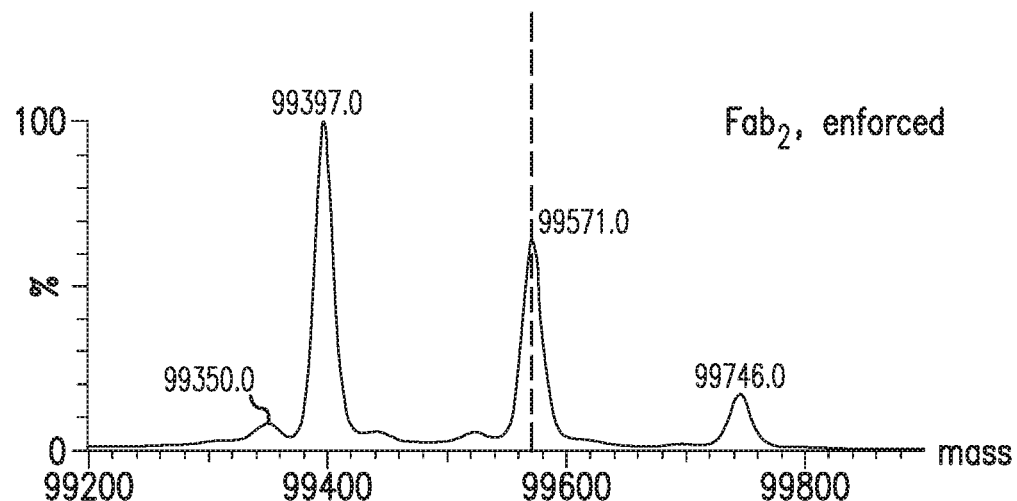
FIG. 4C is a graph showing results for $Fab_2$ treated with glucuronic acid.
Figure 4D:
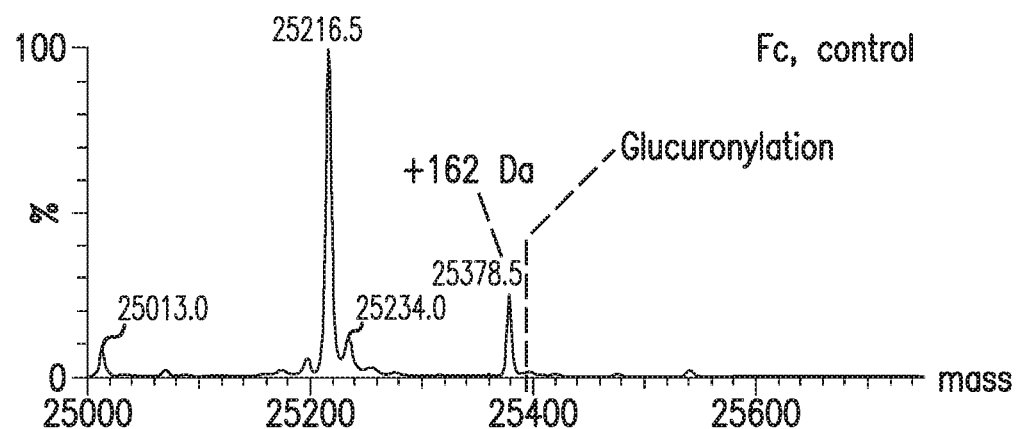
FIG. 4D is a graph showing results for Fc control.
Figure 4E:
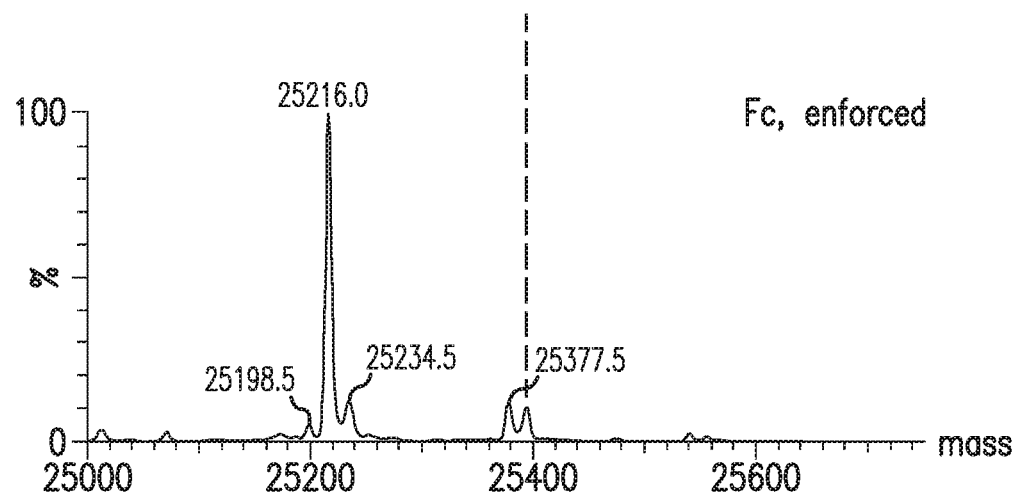
FIG. 4E is a graph showing results for Fc treated with glucuronic acid
Figure 5A:
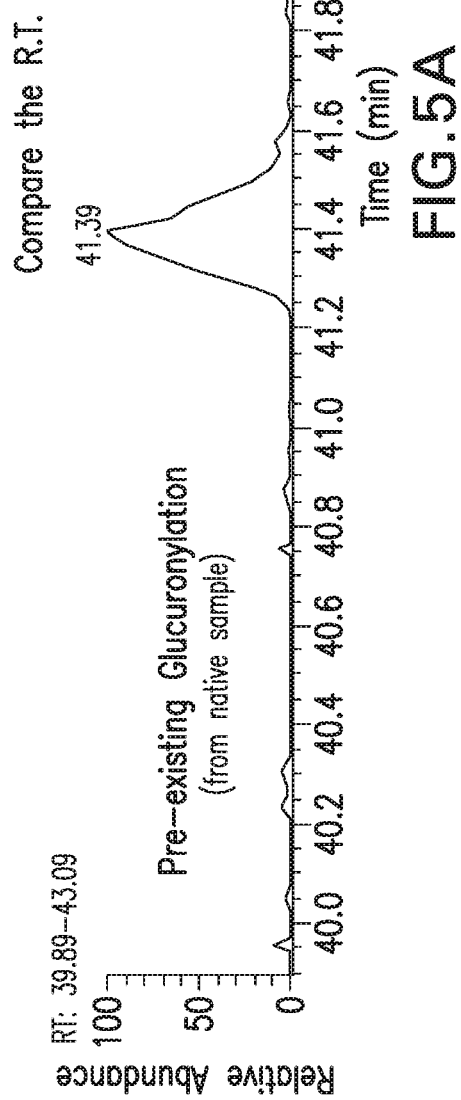
FIG. 5A is a chromatogram from a native sample showing pre-existing glucuronylation.
Figure 5B:
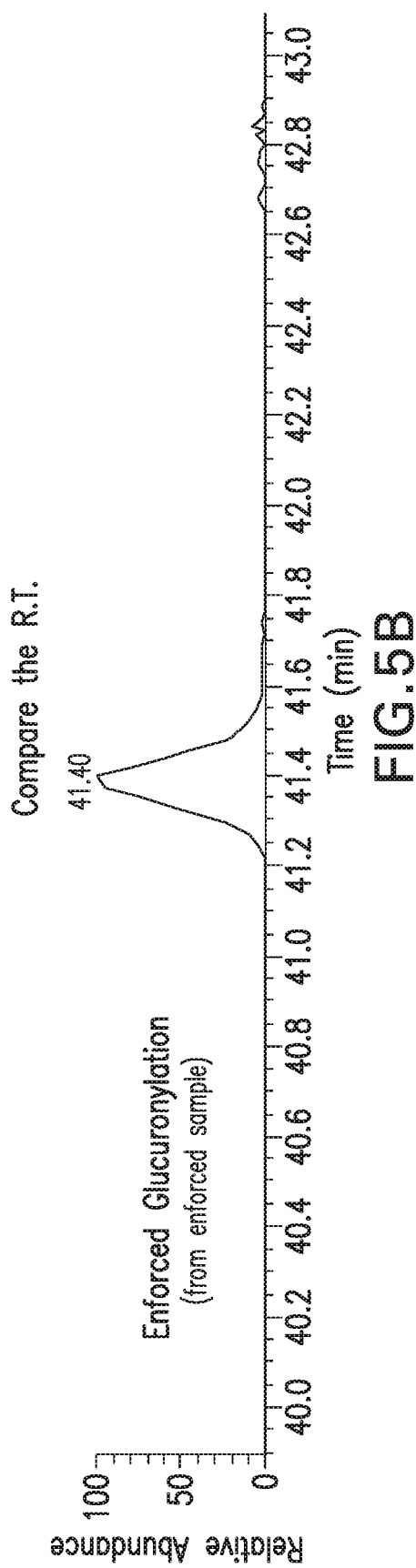
FIG. 5B is a chromatogram from a sample treated with glucuronic acid showing forced glucuronylation.
Figure 5C:
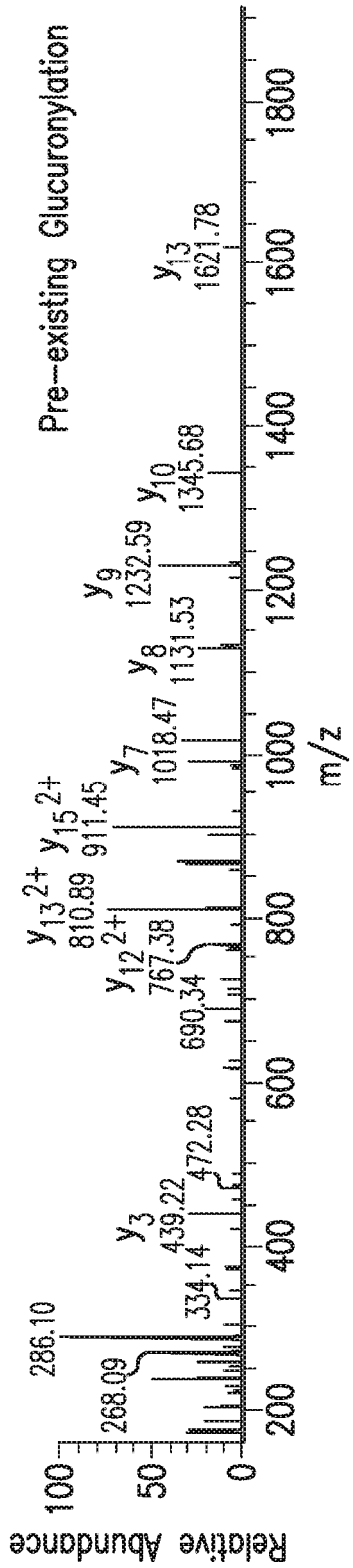
FIG. 5C shows the results of M2 fragmentation patterns for pre-existing glucuronylation.
Figure 5D:
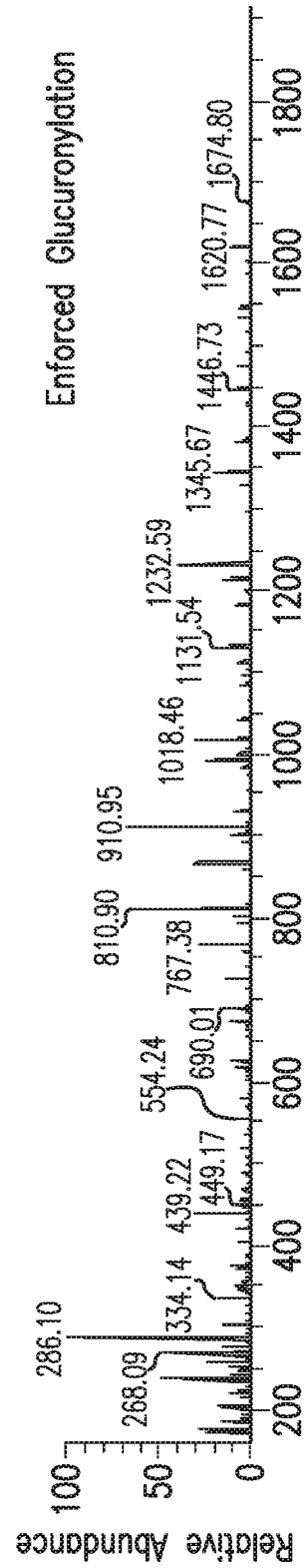
FIG. 5D shows the results of M2 fragmentation patterns for samples treated with glucuronic acid.
Figure 6C:
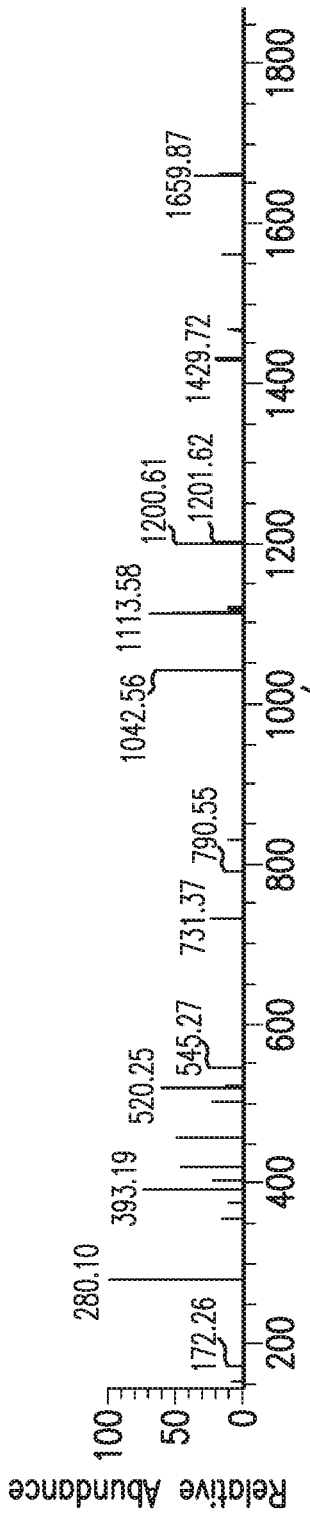
FIG. 6C shows the results of M2 fragmentation patterns for pre-existing glucuronylation.
Figure 6D:
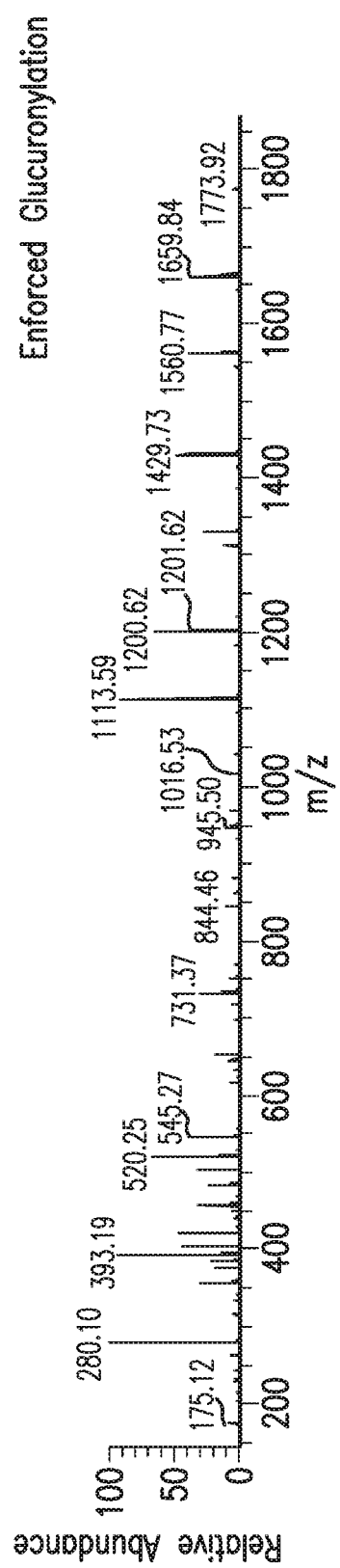
FIG. 6D shows the results of M2 fragmentation patterns for samples treated with glucuronic acid.

The trypsin digested acidic fraction was incubated with 50 mM $NaBH_4$ at 37° C. for 1 hour before quenching with 10% formic acid (FA). The $NaBH_4$ treated sample was then subjected to RP LC/MS analysis. The result showed that this modification (+176 Da) can be reduced (+178 Da) by $NaBH_4$, suggesting the presence of a Schiff base structure in the modification (FIGS. 3A-3B).

Forced glucuronylation was performed by incubating the mAb sample with 100 mM glucuronic acid at 37° C. for 24 hours. Subsequent trypsin digestion and peptide mapping analysis showed that a series of glucuronylated peptides, presenting at much higher abundance in forced modification samples, displayed the same accurate masses. MS2 fragmentation patterns, and retention times as those found in the untreated sample (FIGS. 4A-4E, 5A-5D, 6A-6D, and 7A-7D).

I claim:

1. A method for identifying glucuronylation of a protein drug product comprising
    deglycosylating the protein drug product;
    treating the deglycosylated protein drug product to produce one Fc* fragment comprising two identical Fc/2 fragments bound together through non-covalent interactions, and one Fab2 fragment comprising one Fab2 fragment;
    separating the Fc* and Fab2 complexes using ion exchange chromatography into acidic fractions of Fc* and Fab2;
    drying and denaturing the acidic fractions;
    alkylating the acidic fractions;
    digesting the acidic fractions with trypsin to form a non-reduced sample;
    incubating a portion of the non-reduced sample with $NaBH_4$ to form a reduced sample; and
    subjecting the reduced sample to reverse phase liquid chromatography/mass spectroscopy analysis to identify glucuronylation of the protein drug product.

2. The method of claim 1, further comprising the step of comparing mass spectroscopy analysis between the reduced sample and the non-reduced sample to identify mass differences between the reduced sample and the non-reduced sample.

3. The method of claim 1, wherein the protein drug product comprises a monoclonal antibody.

4. The method of claim 1, wherein the Fc* and Fab2 fragments are formed using a recombinantly modified form of IdeS from *Streptocoocus pyogenes*.

5. The method of claim 1, wherein the ion exchange chromatography is strong cation exchange chromatography.

6. The method of claim 1, wherein the acidic fractions are alkylated with iodoacetamide.

* * * * *